United States Patent [19]

McNeilly

[11] 4,150,443
[45] Apr. 24, 1979

[54] ANTI-FOGGING SPORTS GOGGLE

[75] Inventor: Michael A. McNeilly, South of Ketchum, Id.

[73] Assignee: Robert E. Smith, Ketchum, Id.

[21] Appl. No.: 885,965

[22] Filed: Mar. 13, 1978

[51] Int. Cl.² .............................................. A61F 9/02
[52] U.S. Cl. ......................................... 2/436; 2/171.3
[58] Field of Search ................ 2/435, 436, 437, 171.3, 2/439, 444, 8, 9

[56] References Cited

U.S. PATENT DOCUMENTS

| | | | |
|---|---|---|---|
| 1,582,785 | 4/1926 | Ratti | 2/437 |
| 2,770,807 | 11/1956 | Taylor et al. | 2/444 |
| 3,160,735 | 12/1964 | Aufricht | 2/435 |
| 3,353,191 | 11/1967 | Dahly | 2/171.3 |
| 3,735,423 | 5/1973 | Droz | 2/171.3 |
| 3,825,953 | 7/1974 | Hunter | 2/437 |

Primary Examiner—Peter Nerbun
Attorney, Agent, or Firm—Flehr, Hohbach, Test, Albritton & Herbert

[57] ABSTRACT

A sports goggle provided with power means in the form of a miniature electrical fan mounted within the air space defined by the goggle and the face of the wearer when the goggle is in place. The fan is selectively actuatable by the wearer of the goggle to draw the warm humid air within the air space into the fan, to compress the same therein, and to circulate the same throughout the air space to prevent condensation build-up on the inner surface of the lens structure of the goggle and on eyeglasses of the wearer of the goggle. The fan also urges the circulated warm humid air outwardly of the goggle through air passages provided in the shell of the goggle so that ambient air may enter the goggle to replace the forced out air without admitting snow or other precipitation from the ambient.

13 Claims, 5 Drawing Figures

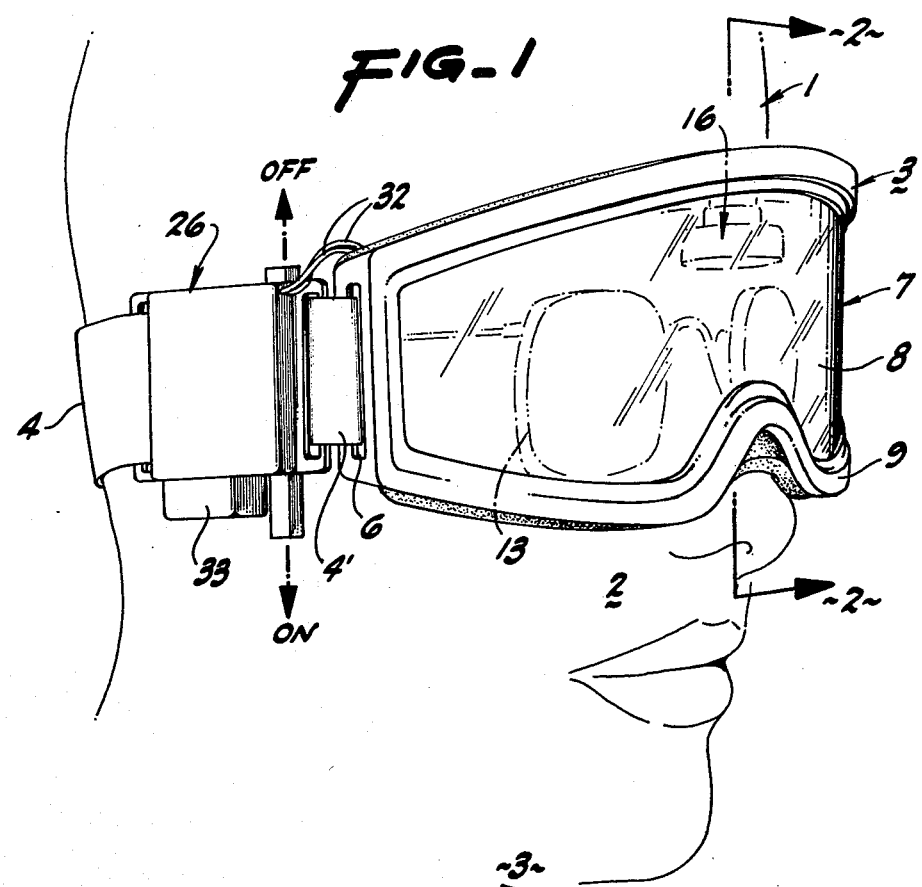
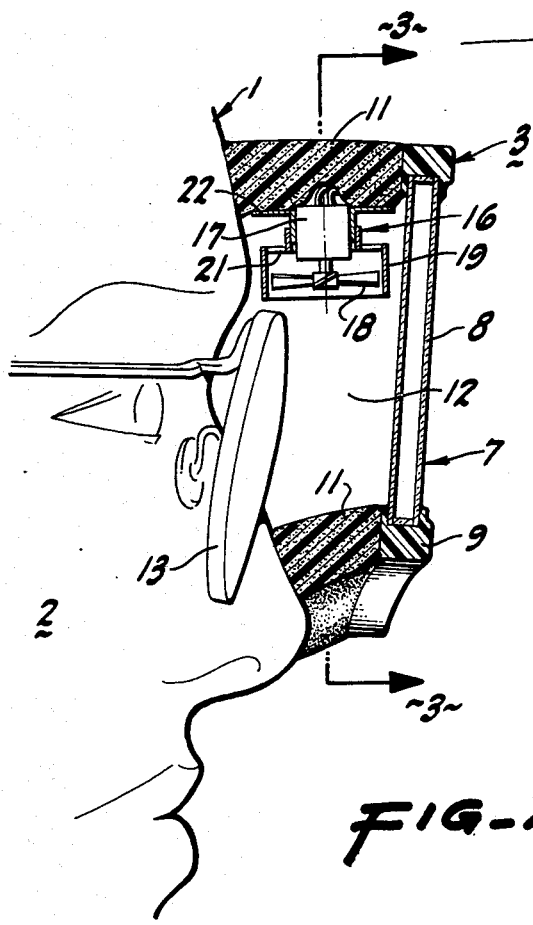

ANTI-FOGGING SPORTS GOGGLE

BACKGROUND OF THE INVENTION

1. Field of the Invention

This invention relates to the field of sports goggles. More particularly, this invention relates to the field of goggles to be worn during winter sporting events such as skiing, and during other cold weather activities. Still more particularly, this invention relates to the field of sports goggles for use outdoors during cold weather which include means for preventing condensation build-up within the goggle so that the lens of the goggle may be maintained free of fog-type condensation and so that the eyeglasses of the wearer of the goggle may also be maintained fog-free. To that end, this invention relates to a sports goggle which includes power means for forcibly circulating air within the air space defined by the goggle and the face of the wearer to prevent the formation of condensation on the inside of the lens structure of the goggle or on the glasses of the wearer of the goggle due to the presence of warm humid air within the goggle.

2. Description of the Prior Art

Sports goggles intended for use during winter activities, such as skiing and the like, are widely known and widely utilized by sports enthusiasts and others whose duties or activities require them to be outside in snowy and other inclement cold weather conditions.

Illustrative of one type of sports goggle which effectively counters adverse weather conditions is the goggle illustrated in Smith U.S. Pat. No. 3,377,626 "Insulated Goggles" dated Apr. 16, 1968. The goggle illustrated and described in said Smith patent also has a counterpart which is commercially available through applicant's assignee, Robert E. Smith of Sport Optics of Ketchum, Idaho, in which the lens structure of the goggle is electrically heated from a small battery power pack carried on the goggle. Both the goggle of the Smith patent and of the heated embodiment also commercially available through applicant's assignee effectively perform their intended purpose.

Other prior art constructions which are intended by their inventors to obviate or minimize the problems of condensation build-up on glasses, goggles or other optical devices which are subjected to inclement and cold weather usage include the patents to De Felice U.S. Pat. Nos. 1,354,433 "Lens Clarifying Apparatus" dated Sept. 28, 1920; Farina 2,526,737 "Combined Goggles and Defogging Device" dated Oct. 24, 1950; Thomas 2,539,284 "Goggles" dated Jan. 23, 1951; Karwowska 2,888,703 "Eyeglass Wiper" dated June 2, 1959; Aufricht 3,160,735 "Anti-Fogging Eyeglasses" dated Dec. 8, 1964; and Rocholl et al, 3,495,259 "Electrically Heated Optical Device" dated Feb. 10, 1970.

None of the patents noted above discloses an anti-fogging sports goggle having the improved features disclosed and claimed herein in that none discloses or suggests the utilization of the unique anti-fogging construction developed by applicant. That is, none of the prior art devices discloses or suggests the utilization of condensation preventing power means defined by a miniature electric motor and fan unit mounted within the air space defined by the lens structure of the goggle and the closure means surrounding the lens structure which contacts the face of the wearer when the goggle is in position. It is such motor and fan unit which effectively compresses and circulates the warm humid air contained in the air space throughout such air space to prevent condensation of moisture on the inner surface of the lens structure and on the glasses of the wearer of the goggle if the wearer utilizes glasses during his outdoor sports activities.

The Smith patent discloses a dual lens structure which is designed to prevent goggle fogging. The other commercial embodiment of the goggle marketed by applicant's assignee heats the lens structure to obviate fogging.

The De Felice patent discloses a squeezable bulb connected to glasses or goggles to direct ambient air against the inside and outside of the lenses. The Farina patent discloses a mouth actuated exhaust structure for sucking air out of goggles when the wearer blows through the mouth piece attached to the goggles to actuate the suction device. The Thomas patent discloses an air heating and circulating unit for circulating warm air through a goggle structure which is actuated by bellows structures mounted in a vest structure worn by the wearer of the goggles. The Karwowska patent discloses eyeglass structure with miniature wiper blades which remove moisture from the outer surface of the eyeglasses in response to actuation of a battery operated electric motor mounted on the eyeglasses. The Aufricht patent discloses a structure for electrically heating the lenses of eyeglasses by a battery power source carried in the frames of the eyeglasses; some air circulation behind the lenses is increased due to movement of heated air therebehind. Finally, the Rocholl et al, patent discloses an electrical heating arrangement to prevent fogging on the external surface of an optical device, such as a telescope.

As noted, none of the patents referred to above, nor applicant's assignee's electrically heated lens goggle structure, discloses or suggests the utilization of the particular air circulation power means and anti-fogging construction disclosed and claimed herein.

SUMMARY OF THE INVENTION

This invention relates to an improved sports goggle. More particularly, this invention relates to an anti-fogging sports goggle which incorporates in its structure improved means for precluding the deposition of condensation on the inner surface of the lens structure of the sports goggle and, with respect to those situations where the wearer of the goggle also wears eyeglasses, upon the lenses of the glasses of the wearer. Still more particularly, this invention relates to an improved anti-fogging sports goggle in which power means defined by a miniature electrical motor and fan unit is selectively positioned within the air space defined between the lens structure of the goggle and the face of the wearer, the purpose of which is to compress and circulate the moist warm air within the air space to prevent condensation build-up on the inner surface of the goggle lens structure and on the lenses of eyeglasses of the wearer of the goggle. Such motor and fan unit also urges the moist warm air outwardly of the goggle air space to permit ambient air to replace the same under controlled conditions.

Prior to applicant's invention, attempts to prevent fogging of sports goggles and related optical devices generally centered upon heating of the lenses of the goggle; directing ambient air against the lenses of the goggle both internally and externally thereof; and attempting to exhaust the air from within the air space defined by the goggle and the face of the wearer; in the manner disclosed in the prior art discussed hereinabove. However, none of the prior art patents with which applicant is familiar discloses or suggests the use of positive pressure producing power means positioned within the air space defined by the goggle and the face of the wearer to selectively circulate the humid warm air within the air space throughout that air space to prevent its condensation on the inner surface of the goggle lens structure. Nor does any of the prior art referred to above and with which applicant is familiar direct itself to solution of the problem of fogging of the eyeglasses of the wearer of the goggles which are positioned in the air space defined by the goggle. That is, no prior art specifically attacked the problem of keeping the wearer's eyeglasses fog free at the same time the goggle lense structure is maintained fog free.

Accordingly, objects of this invention include the provision of an improved anti-fogging sports goggle; the provisions of such an improved sports goggle which includes means to prevent fogging of the goggle lense structure and also of the glasses of the wearer of the goggles; the provision of improved means for forcibly circulating the moist warm air within the air space defined by the goggle and the face of the wearer to prevent condensation build-up by creating a positive pressure within the air space; and the provision of an improved sports goggle which has positioned in the air space defined by the goggle and the face of the wearer a miniature electrical motor and fan unit which selectively and forcibly circulates air within the air space to prevent fogging when the power source for the fan is selectively actuated by the wearer of the goggle.

These and other objects of this invention will become apparent from the following description when taken in conjunction with the accompanying drawings.

DESCRIPTION OF THE DRAWINGS

FIG. 1 is a perspective view of the improved anti-fogging sports goggles of this invention shown positioned on the head of the wearer over eyeglasses worn by the wearer.

FIG. 2 is a side view of the head of the wearer with the goggle shown in vertical section taken generally in the plane of line 2—2 of FIG. 1.

DESCRIPTION OF THE PREFERRED EMBODIMENT

Figure 3:
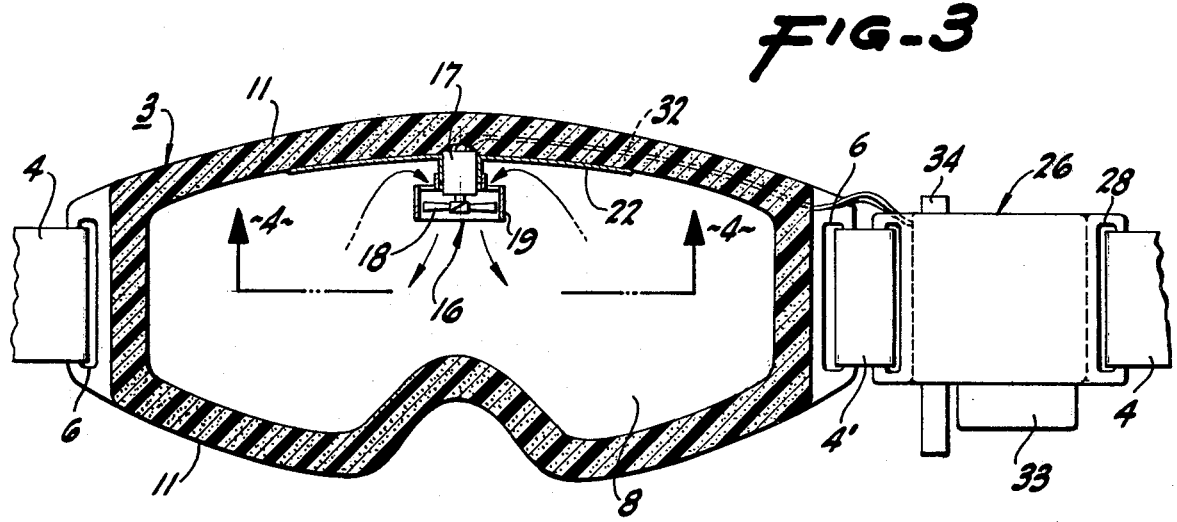
FIG. 3 is a vertical sectional view in the longitudinal direction of the goggle taken generally in the plane of line 3—3 of FIG. 2.

In its preferred embodiment, the present anti-fogging sports goggle is a variation of and improvement upon the goggle illustrated in Smith U.S. Pat. No. 3,377,626 referred to above. In its preferred form, as described hereinafter, the present goggle desirably utilizes the lens structure and closure means of said Smith patent which defines the air space provided between the lens structure and the face of the wearer when the goggle is in position.

To such basic goggle structure as shown in said Smith patent is added means to forcibly circulate the moist warm air found within the air space in front of the wearer's face when the goggle is positioned on the head of the wearer, and electrical source means to selectively actuate said air circulating means in response to defogging requirements confronted by the wearer of the goggle.

Referring to FIG. 1 the head of the wearer of the goggle is generally identified by reference numeral 1 with the face of the wearer identified by reference numeral 2. Applicant's improved sports goggle is generally designated 3 and, as shown in FIG. 1, is intended to be positioned over the eyes of the wearer to enclose at least a portion of the wearer's forehead, eyes and nose in known fashion.

Similarly, in known fashion, the goggle includes an adjustable strap structure generally designated 4,4' which is operatively connected with slots 6 in opposite sides of the frame of the lens structure 7 of the goggle in known fashion. The strap structure surrounds the heads of the wearer of the goggle to maintain the goggle securely in place during strenuous outdoor cold weather activities, such as skiing.

The goggle lens structure 7 is preferably of the type disclosed in Smith U.S. Pat. No. 3,377,626; such lens structure includes colored or clear dual lenses of plastic or other suitable transparent material, collectively designated 8, and a lens frame designated 9 in which the periphery of the lenses 8 is molded or otherwise secured.

The goggle also includes closure means in the form of a resilient but generally rigid shell, designated 11. The closure shell preferably is formed of a one piece molding of a rubber foam or other flexible polymeric foam material which is air pervious. The foam material is selected to provide comfort to the wearer but also is selected from a material which possesses sufficient rigidity and body to permit the goggle to withstand the stresses and strains of vigorous sports activities. Although not shown in the drawings, if desired the foam shell may have a thin inner layer of soft foam or other padding adhered thereto to further enhance the comfort of the goggle wearer when the goggle is in place against the wearer's face.

If necessary, the frame of the lens structure may be extended inwardly about the entire periphery of the goggle and narrow supporting ribs (not shown) may be added to the foam shell to increase the strength thereof as may be required. However, such supporting ribs and lens frame extensions are not illustrated because such structure is not necessary if the proper foam material is selected.

The foam material chosen for closure shell 11 has sufficient permeability to permit forced passage of air through the foam material under the defogging conditions described hereinafter.

As perhaps best seen in FIG. 2, the lens structure 3 combines with the foam shell 11 to define an air space between the lens structure and shell and face of the wearer when the goggle is in place. That air space is generally designated 12 in FIG. 2. The closure shell 11 is of sufficient thickness to insure that the air space 12 is large enough to accommodate therein a pair of eyeglasses, designated 13, should the wearer's vision dictate the use of eyeglasses or should weather conditions prescribe the use of some form of additional visual assistance.

The utilization of eyeglasses by the wearer of the goggle of this invention dictates one of the principal purposes for the particular invention set out herein, namely the defogging of the eyeglasses of the wearer in conjunction with defogging of the inner surface of the lens structure 3 of the goggle.

Thus, it should be understood from FIGS. 1 and 2 that when the goggle is properly positioned on the head of the wearer that the goggle totally shields the face area of the wearer surrounding the eyes and fully covers and protects a pair of eyeglasses worn by the wearer.

The improvement of the present invention resides specifically in the inclusion in a sports goggle of power means to selectively circulate the moist warm air which builds up in the air space 12 when the goggle is in use. Such circulation is effected to prevent condensation build-up on the inner surface of the lens 8 of the goggle and on the lenses of the eyeglasses 13 of the wearer of the goggle. Such circulation is effected in the present invention by means designed to create a positive pressure in the air space 12 within the goggle, the purpose of which is to circulate the moist warm air as described and also to effect the expelling of such moist warm air in slow controlled fashion through the permeable foam shell 11 which defines the air space 12 with lens structure 3. When the moist warm air is expelled from the air space, ambient air similarly may pass through the permeable foam shell 11 to replace the forced out air.

The means employed for the intended purpose of controlled circulation of moist warm air in the air space in the present embodiment includes a miniature electrical motor and fan unit 16 which is mounted on the goggle within the air space 12 but in such a location and position that it does not impair the vision of the wearer of the goggle or interfere with the wearer's ability to wear eyeglasses as previously described. To that end, the motor and fan unit 16 preferably is mounted in depending relationship from the top of the foam shell 11 generally centrally thereof; that is, generally in a location between the eyes of the wearer where the motor and fan unit is least likely to be noticed by the wearer. Locating the fan in the position described has the additional advantage of producing most effective air circulation within the air space 12 because of the central location thereof. However, under other circumstances, other motor and fan unit mounting locations may be employed and, under certain circumstances, it may be desirable to utilize more than one miniature motor and fan unit of the type described positioned at selected opposing locations within the air space 12.

In that latter regard, the motor and fan unit 16 chosen is a commercially available unit which is about one inch in total length and approximately one inch in outer diameter. As will be described, the electrical motor which forms part of the motor and fan unit 16, by way of example, is a six volt motor which operates at approximately 12,500 r.p.m. A conventional nine volt battery of the type used in transistor radios and other electrical appliances is a suitable electrical power source. The motor and fan unit of the type described is capable of circulating two to four cubic feet of air per minute within the air space 12 of the goggle.

The electrical motor of the motor and fan unit is designated 17 while the fan itself is designated 18. Preferably the blades of the fan are surrounded by a depending shroud designated 19 which is connected in laterally spaced concentric relationship to the housing of the motor by a series of thin spaced depending connecting ribs 21, as perhaps best seen in FIGS. 3 and 4.

Figure 4:
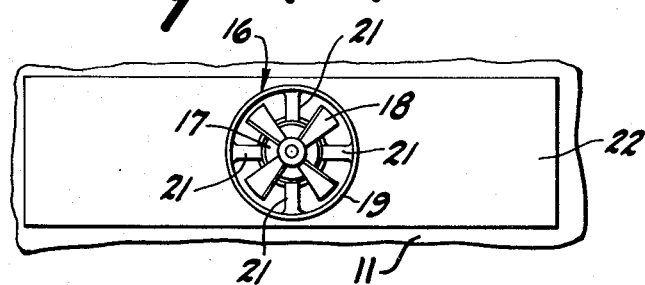
FIG. 4 is a partial plan view of the goggle looking in the direction of line 4—4 of FIG. 3 and illustrating the motor and fan unit of the subject invention and the mounting plate by means of which the motor and fan unit are secured to the goggle.

As seen in FIG. 4, the motor and fan unit 16 is mounted to depend from the top of the foam shell 11 by means of a generally rectangular plastic plate 22 which is adhesively or otherwise suitably secured to the inside surface of the top of the foam shell. The plate extends for a predetermined distance, such as an inch and one half in each direction, from the center of the electric motor 17 and is dimensioned to fill in the entire top portion of the foam shell so that air may not enter or exit through the shell 11 in immediate proximity to the fan.

Thus, the plate 22 serves the dual purpose of mounting the motor and fan unit 16 in depending relationship from the top of the foam shell as described and also preventing the introduction of ambient air directly through the foam shell downwardly into the shroud 19 surrounding the fan 18. It has been found preferable to prevent ambient air from being drawn directly into the fan because to do so increases the fogging problems within the air space 12. Thus, the plate 22 insures that the air circulated by the fan 19 within the air space is drawn primarily from the warm moist air already in the air space rather than being drawn directly from the outside ambient air. The air flow pattern through the fan is generally shown by the arrows in FIG. 3.

When the fan operates, the warm moist air within the air space is circulated throughout the full air space as a result of compression of the air by the fan and movement thereof by the fan prior to its discharge from the shroud 19 surrounding the fan. Thus, a positive pressure is created within the air space in the goggle which results in the warm moist air being actively circulated within the air space while it is also slowly forced out of the air space through air passages in the pervious foam shell 11, to be replaced at a generally equal rate by ambient air from outside the goggle. Such replacement is effected in controlled conditions depending upon selective activation of the fan by the wearer of the goggle so that fogging problems within the goggle are not compounded by ambient air rushing unrestricted into the goggle.

Figure 5:
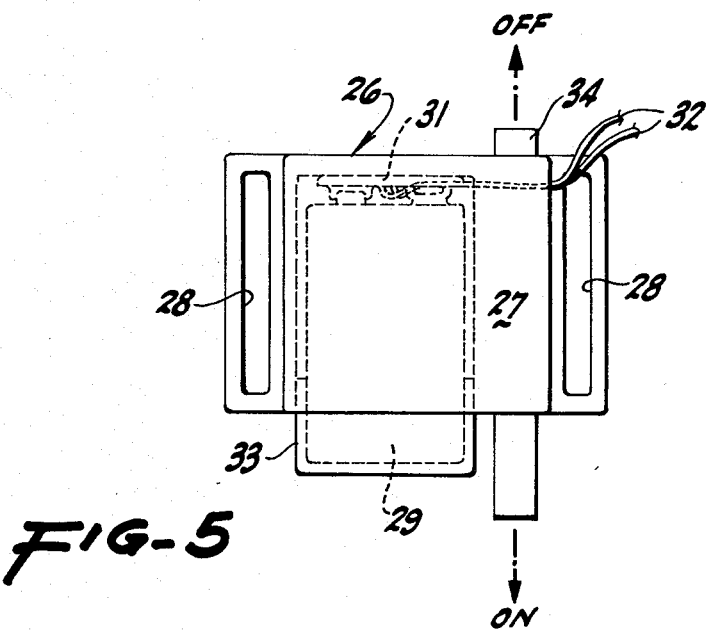
FIG. 5 is a side elevational view of the battery pack power source used to selectively activate the motor and fan unit.

Provided in conjunction with the goggle is an electrical power source operatively connected with the motor and fan unit 16 to selectively actuate the motor and drive the fan in accordance with defogging requirements confronted by the wearer. Such power source includes a battery power pack designated 26 which preferably is mounted adjacent the lens structure of the goggle and is carried by the strap means 4,4' thereof. To that end, the casing 27 of the power pack 26 is provided with slots 28 along each edge thereof through which the strap 4 and strap link 4' may pass in known fashion. Within the power pack, as shown in dotted lines in FIG. 5, is a conventional nine volt battery 29, the positive and negative poles of which have engaged therewith a connector 31 from which electrical lead wires 32 extend to the electric motor 17 and which are connected thereto in known fashion. Preferably the lead wires 32 are adhesively secured to the inner surface of the foam shell 11 of the goggle and are securely held in place therealong. As required, the battery 29 may be replaced in known fashion by pulling downwardly on the battery carrier portion 33 of the power pack 26 which is snap locked in place in the power pack in known fashion.

Provided on the battery power pack is a manually actuatable on-off switch 34 which is selectively movable in the vertical direction, downwardly to activate the motor and fan unit and upwardly to deactivate the same, in the manner illustrated in FIGS. 1 and 5.

The battery power pack is a commercially available unit marketed by the Sierracin Corporation, 12780 San Fernando Road, Sylmar, Calif. 91342.

Thus, it will be understood that, depending upon the weather conditions confronted by the wearer of the goggle, the electric motor 17 and fan 18 may be continuously activated during a ski run or like outdoor activity, or the same may be selectively activated when fogging of the goggle or the glasses of the wearer is noted. It is not necessary for the wearer of the goggle to stop his activity, such as the ski run in which he is engaged, to activate the defogging motor and fan unit 16 because it is merely necessary for him to depress the control switch 34 to the on position as shown in FIG. 5 even when he is engaged in his activity.

Thus, from the foregoing, it will be understood that this invention incorporates into an anti-fogging sports goggle power means in the form of an electric motor and fan unit which is selectively actuatable from a battery power pack carried by the goggle to forcibly circulate air within the internal air space surrounding the eyes of the wearer of the goggle to prevent fogging of the inner surface of the goggle lens structure and the lenses of the eyeglasses of the wearer. Such defogging is effected because the motor and fan unit create a positive pressure within the air space which forcibly and effectively circulates air within the goggle and also controllably expels warm moist air from the goggle as required to prevent the undesirable fogging condition noted.

Reference is directed to the appended claims for the scope of protection to be afforded this invention with reference being taken to the appended description and drawings for an understanding thereof.

I claim:

1. An anti-fogging sports goggle comprising a lens structure sufficiently wide to span the eyes of the wearer, closure means in conjunction with said lens structure to position said lens structure a sufficient distance from the eyes of the wearer to permit the wearer to wear eyeglasses beneath the goggle in the air space between the lens structure and the face of the wearer, strap means to removably maintain the goggle in position on the wearer's head, and a motor and fan unit carried directly on and forming part of the goggle without projection exteriorly therefrom to forcibly circulate the moist warm air present in said air space over the glasses of the wearer and over the inner surface of said lens structure to preclude condensation build-up on said glasses and on said inner surface of said lens structure; said motor and fan unit being integral with said goggle and mounted directly thereon to preclude the entry of ambient air directly therethrough into said air space.

2. The sports goggle of claim 1 in which said motor and fan unit includes a miniature electric fan mounted on said goggle and extending into said air space to effect said air circulation within said air space; said motor and fan being generally isolated from the ambient air when said goggle is positioned on the face of the wearer so that air, snow and ambient moisture are blocked from direct entry into said air space.

3. The sports goggle of claim 2 in which an electric power source is operatively connected with said motor which drives said fan, and switch structure in conjunction with said power source for selectively activating and deactivating said fan in accordance with defogging requirements.

4. The sports goggle of claim 3 in which said power source constitutes a battery pack carried adjacent said lens structure on said strap means, and electrical wires leading from a battery in said battery pack to said motor.

5. The sports goggle of claim 3 in which said motor and said fan are mounted as an integral unit generally centrally of said lens structure within said air space in depending relationship from the top of said closure means.

6. The sports goggle of claim 5 in which said motor and fan unit is secured to an elongated air impervious plate which is secured to the inside of said top of said closure means, said plate precluding the introduction of ambient air directly into said fan from outside said goggle so that air within said air space is first drawn into said fan and compressed therein before circulation thereby into said air space.

7. An anti-fogging sports goggle comprising a lens structure sufficiently wide to span the eyes of the wearer, closure means connected with said lens structure to position said lens structure from the eyes of the wearer a distance sufficient to permit the wearer to wear eyeglasses beneath the goggle in an air space created by said closure means and said lens structure, strap means to removably maintain the goggle in position on the wearer's head, a battery power pack carried by said strap means, a miniature motor and fan unit integral with and supported by said closure means and positioned within said air space so that no portion thereof projects from said goggle, electrical wires operatively connecting said motor with said power pack, and switch means in conjunction with said power pack for selectively activating and deactivating said motor and fan unit in accordance with defogging requirements, the fan of said motor and fan unit when activated drawing warm humid air present in said air space through said fan and compressing the same and thereafter forcibly circulating the same around in said air space to preclude condensation build-up on the eyeglasses of the wearer and on the inner surface of said lens structure without directly drawing ambient air and ambient moisture through said motor and fan unit from outside said goggle when said goggle is on the face of the wearer.

8. The sports goggles of claim 7 in which said closure means is pervious to ambient air and to said moist humid air within said air space so that said moist humid air within said air space may be forced out of said goggle and ambient air may enter said air space through said closure means, but without admitting snow or other ambient precipitation, to replace said forced out air when said motor and fan unit is operating.

9. The sports goggle of claim 8 in which said closure means comprises a foam material which is permeable to air but which is generally impervious to snow and other precipitation so that the air space in said goggle remains free of ambient moisture when positioned over the eyes of the wearer.

10. The sports goggle of claim 8 in which said motor and fan unit is enclosed within said goggle and is secured in depending relationship from the top of said closure means generally centrally thereof but without impairing the vision of the wearer and without interfering with the eyeglasses worn by the wearer.

11. A sports goggle having a lens structure, closure means to be engaged with the face of the wearer and surrounding the lens structure, said closure means defining an air space with said lens structure when the goggle is positioned across the eyes of the wearer, a miniature electric motor and fan unit forming an integral part of and mounted on said goggle within said air space without impairing the vision of the wearer, and electrical power means in conjunction with said goggle operatively connected with said motor and fan unit to drive said fan thereof to positively circulate air present within said air space to preclude fogging within said goggle, said motor and fan unit being generally isolated by said closure means from the ambient air to preclude the entry of snow and other precipitation through said unit into said air space.

12. The sports goggle of claim 11 which includes switch means in conjunction with said electrical power means to selectively activate and deactive said motor and fan unit in response to defogging requirements.

13. The sports goggle of claim 11 in which said motor and fan unit is mounted in said air space in depending relationship from the top of said closure means generally centrally thereof in a location generally between the eyes of the wearer.

* * * * *